United States Patent [19]

Jones

[11] Patent Number: 5,158,082
[45] Date of Patent: Oct. 27, 1992

[54] APPARATUS FOR HEATING TISSUE WITH A PHOTOPLETHYSMOGRAPH SENSOR

[75] Inventor: Paul H. Jones, Mercer Island, Wash.
[73] Assignee: SpaceLabs, Inc., Redmond, Wash.
[21] Appl. No.: 573,342
[22] Filed: Aug. 23, 1990
[51] Int. Cl.⁵ .............................................. A61B 5/00
[52] U.S. Cl. ..................................... 128/633; 356/41; 128/666
[58] Field of Search .................... 128/633, 665, 666; 356/41

[56] References Cited

U.S. PATENT DOCUMENTS

| | | |
|---|---|---|
| 4,259,963 | 4/1981 | Huch . |
| 4,714,080 | 12/1987 | Edgar, Jr. et al. ................. 128/666 |
| 4,723,554 | 2/1988 | Oman et al. ........................ 128/633 |
| 4,926,867 | 5/1990 | Kanda et al. ....................... 128/633 |
| 5,007,423 | 4/1991 | Branstetter et al. .............. 128/633 |

FOREIGN PATENT DOCUMENTS

| | | |
|---|---|---|
| 0040416 | 11/1981 | European Pat. Off. . |
| 0329196 | 8/1989 | European Pat. Off. . |
| 3711272 | 10/1987 | Fed. Rep. of Germany ...... 128/633 |
| 2050615 | 1/1981 | United Kingdom . |
| 2055476 | 3/1981 | United Kingdom . |

OTHER PUBLICATIONS

Mendelson et al., "Nonivasive Pulse Oximetry Utilizing Skin Reflectance Photoplethysmography," IEEE Transactions of Biomedical Engineering, Oct. 1988, pp. 798–805.
Noninvasive Pulse Oximetry Utilizing Skin Reflectance Photoplethysmography, *IEEE Transactions on Biomedical Engineering*, vol. 35, No. 10, Oct. 1988, Yitzhak Mendelson and Burt D. Ochs.

*Primary Examiner*—Kyle L. Howell
*Assistant Examiner*—Robert L. Nasser, Jr.
*Attorney, Agent, or Firm*—Seed and Berry

[57] ABSTRACT

A method and apparatus for increasing the blood flow in a patient's tissue by warming the tissue with heat generated by a semiconductor device mounted in a sensor. The amount of heat generated is controlled by varying either the magnitude or the duty cycle of the current that flows through the semiconductor device, with the amount of heat required determined by either the temperature of the sensor's contact surface or the operating performance of the apparatus.

9 Claims, 5 Drawing Sheets

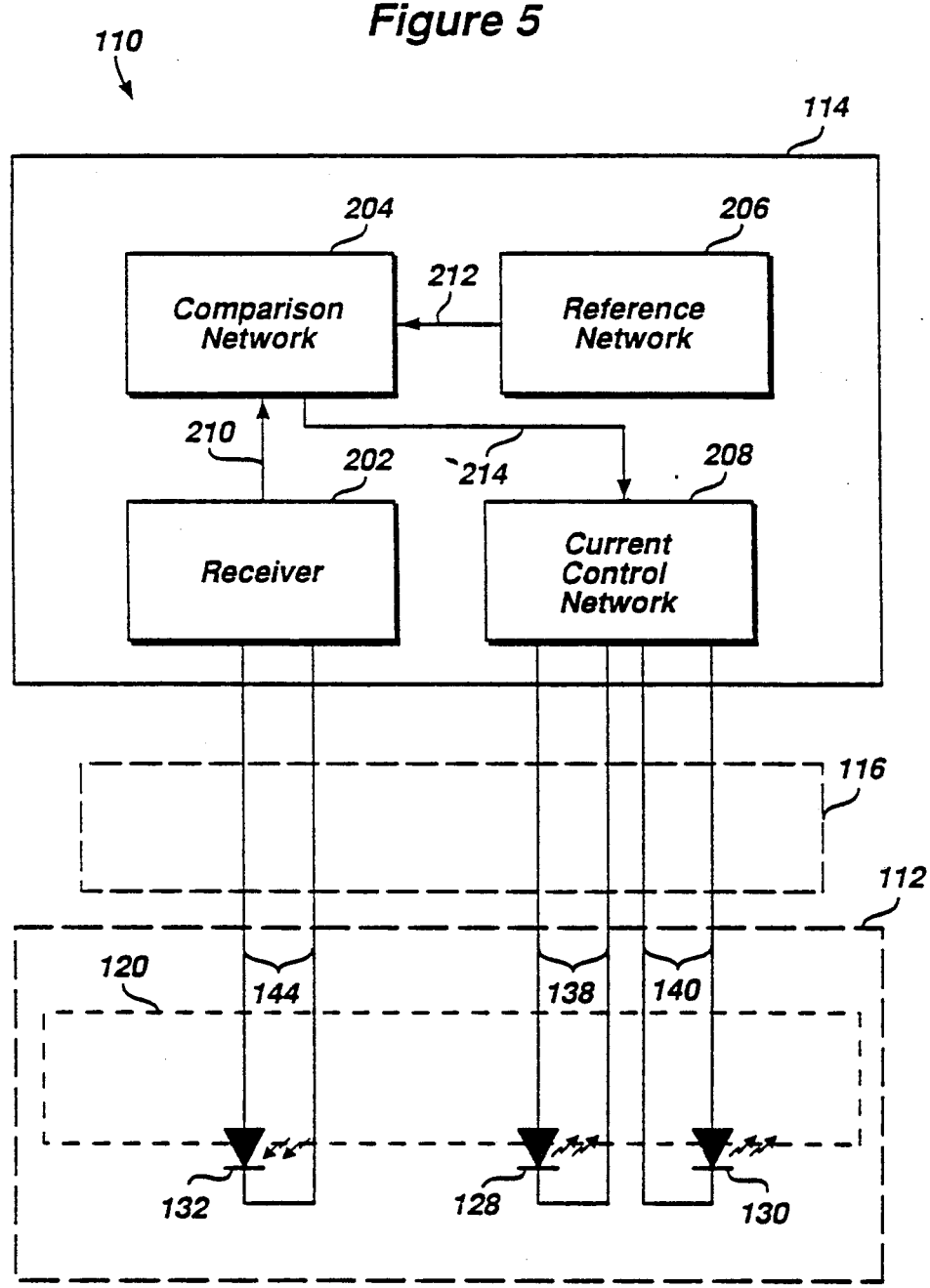

5,158,082

APPARATUS FOR HEATING TISSUE WITH A PHOTOPLETHYSMOGRAPH SENSOR

DESCRIPTION

1. Field of the Invention

This invention relates to a method and apparatus for increasing blood circulation. More particularly, it relates to a system for warming tissue using heat generated in a semiconductor device, thereby increasing blood circulation.

2. Description of the Prior Art

Photoplethysmographs are well known instruments for determining and registering variations in the blood present or passing through tissue using light. A specific application of a photoplethysmograph is in non-invasive pulse oximetry, the measurement of arterial hemoglobin oxygen saturation.

Pulse oximeters typically utilize two light sources, generally red and infrared light-emitting diodes (LEDs), that emit light through a patient's skin. The red and infrared light that is reflected from, or alternatively, that passes through, the patient's tissue and blood are detected by a photodetector. The hemoglobin oxygen saturation of the patient's blood is determined from the detected light based upon differences in the absorption coefficients of the red and infrared light by the oxygen in the blood.

For proper operation, a pulse oximeter requires a sufficiently high blood flow that differences in the oxygen absorption coefficients can be measured. Unfortunately, hypothermia (low body temperature) or other conditions can significantly reduce the blood flow in tissue near the patient's skin. It is therefore desirable to increase the flow of blood to enable an accurate measurement. One method of increasing the blood flow is to warm the tissue.

The advantages of localized tissue heating when performing pulse oximetry was shown by Mendelson et al. in the *IEEE Transactions On Biomedical Engineering*, Vol. 35, No. 10, Oct. 1988, in an article entitled "Noninvasive Pulse Oximetry Utilizing Skin Reflectance Photoplethysmography." Mendelson et al. used a round thermofoil heating element to warm a patient's tissue. Mendelson et al. reported a significant increase in the detected light when the patient's skin was warmed. However, adding a separate heating element increases the cost, component count, assembly difficulty, and complexity of the apparatus.

It is well known that semiconductor devices, such as light-emitting diodes, are not 100% efficient. The inefficiency typically manifests itself in the generation of heat, which is usually highly undesirable. Substantially all of the heat generated in a semiconductor device is from its forward biased PN junctions. A forward biased PN junction usually has a relatively constant voltage drop when conducting a wide range of currents. The heat generated, equal to the current through the PN junction times the voltage drop across the junction, is therefore highly dependent upon the current. The heat generated can be controlled by varying the current's magnitude, duty cycle, or both. The generated heat can be conducted away from the PN junction by thermally conductive materials to warm objects.

It is clear that there has existed a need for a simple, low cost, and low component count pulse oximeter that is capable of increasing the blood flow in tissue in contact with a pulse oximeter's sensor. Although the above-described problem has been explained in terms of a photoplethysmographic based pulse oximeter, the principles of the present invention unmistakably may be used in other apparatus.

SUMMARY OF THE INVENTION

It is an object of the present invention to provide an apparatus for increasing blood flow in tissue local to a photoplethysmograph sensor having a light emitter by transferring heat generated in the light emitter to the tissue.

This and other objects of the invention are accomplished by generating heat in a semiconductor device mounted in thermal contact with a heat conductive plate which, in turn, is in contact with a patient's skin. If the invention is part of a pulse oximeter, the semiconductor device is preferably a light-emitting diode.

In the preferred embodiment, the heat generated is controlled to prevent tissue damage while simultaneously providing sufficient heat to increase the blood circulation. Suitable current control methods include varying either the magnitude and/or the duty cycle of the current through the semiconductor device. The amount of heat required can be determined by a temperature sensor, such as a thermistor, in thermal contact with the heat plate or by the strength of the received signals.

BRIEF DESCRIPTION OF THE DRAWINGS

FIG. 5 is a simplified schematic diagram of the embodiment shown in FIG. 4.

DETAILED DESCRIPTION OF THE PREFERRED EMBODIMENTS

Figure 1:
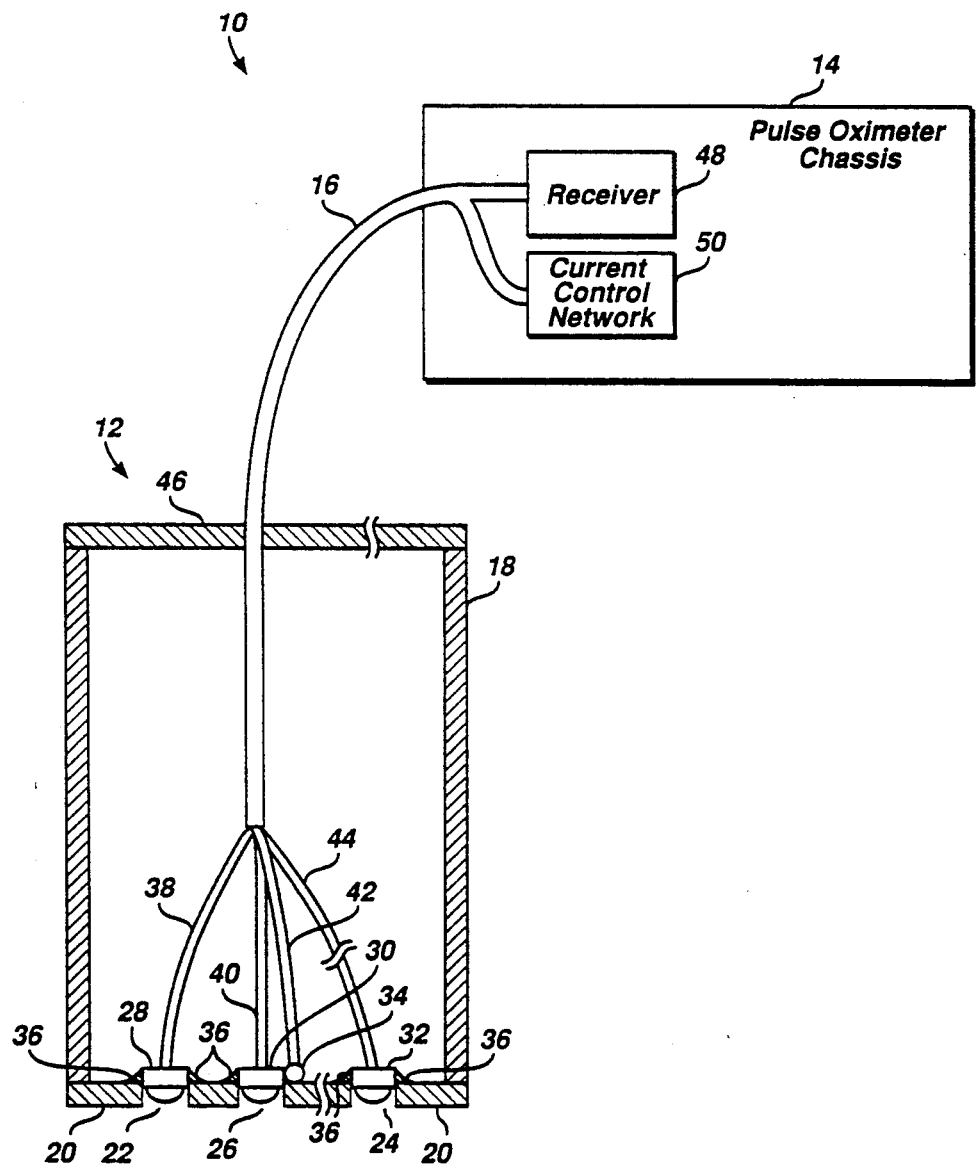
FIG. 1 is a partial cut-away view, partial block diagram of the preferred embodiment.

Referring to FIG. 1, a pulse oximeter 10 is shown that has a transducer 12, a pulse oximeter chassis 14, and a cable 16, all according to the preferred embodiment. The construction and operation of these elements are described in detail below.

The transducer 12 includes a housing 18 with a thermally conductive heat plate 20 as a bottom surface. This heat plate 20 has an IR opening 22, a photodiode opening 24, and a RED opening 26. An IR LED 28 and a RED LED 30 are mounted within the housing 18, in thermal contact with the heat plate 20, and substantially axially aligned with the IR opening 22 and the RED opening 26, respectfully. A silicon photodiode 32 is also within the transducer 12 and is mounted in a substantially axially aligned position with the photodiode opening 24. The silicon photodiode 32 does, but need not, thermally contact the heat plate 20. A thermistor 34 is also mounted within the transducer 12 and in thermal contact with the heat plate 20. While FIG. 1 shows the thermistor 34 abutting the RED LED 30, it may be located elsewhere on the heat plate 20, provided that it can quickly and accurately sense the temperature of the heat plate 20 near the LEDs 28 and 30. The LEDs 28 and 30 are located in close proximity to each other to minimize the differences in the optical paths between the LEDs 28 and 30 and the silicon photodiode 32.

A thermally conductive adhesive compound 36 is applied between the heat plate 20 and the components in thermal contact with the heat plate 20. The adhesive compound 36 assists in heat transfer between the LEDs 28 and 30 and the mounting of the components. The adhesive compound 36 is preferably a thermally conductive epoxy cement such as OMEGABOND 200 from OMEGA Engineering, Inc., Stamford, CT, although other adhesive compounds are usable.

The heat plate 20 can be fabricated from any relatively rigid, heat conductive material, and in any shape suitable for transferring heat to a patient's skin. The heat plate 20 must (1) support the operating components, (2) transfer heat generated in the LEDs 28 and 30 to the patient's skin, and (3) provide sufficient physical contact with the patient's skin to enable pulse oximeter operation. Suitable materials include various grades of aluminium, steel, and brass and suitable shapes are flat, concave, and convex.

Referring again to FIG. 1, the transducer 12 electrically connects to the pulse oximeter chassis 14 via the cable 16. The transducer 12 is hermetically sealed by a seal 46 to protect the components within the transducer 12. Referring now to both FIGS. 1 and 2, the pulse oximeter chassis 14 includes a receiver 48 and a current control network 50. The current control network 50 connects to the IR leads 38, the RED leads 40, and the thermistor leads 42 while the receiver 48 connects to the photodiode leads 44.

Figure 2:
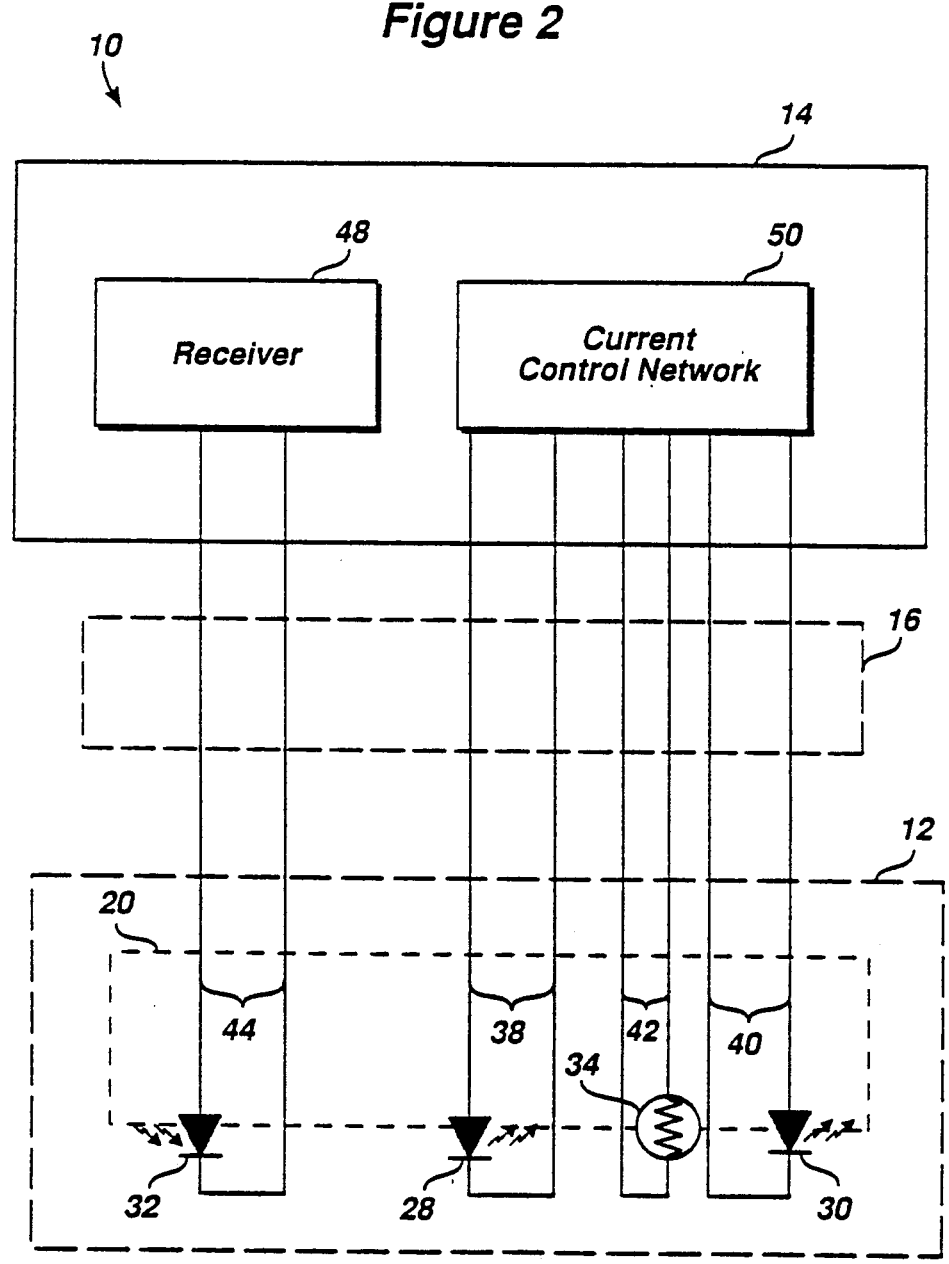
FIG. 2 is a simplified schematic diagram of the embodiment of FIG. 1.

The operation of the preferred embodiment is best understood by referring to FIG. 2 while studying the following discussion. During operation, the heat plate 20 is placed in physical contact with a patient undergoing pulse oximetry. As required for basic pulse oximeter operation, the current control network 50 applies current alternately to the IR LED 28 and the RED LED 30 to cause them to emit light. A portion of the emitted light reflects from the patient's blood and tissue onto the silicon photodiode 32. The silicon photodiode 32 converts its received light into electrical signals used by the pulse oximeter 10 to perform blood oxygen saturation measurements.

The above paragraph describes the light from the LEDs 28 and 30 as being reflected from the tissue and blood. This mode of operation is called the reflective mode. In another mode, the transillumination mode, light from the LEDs 28 and 30 is detected after passing through relatively thin portions of a patient's anatomy, such as an earlobe or a finger. While the present invention is suitable for use with pulse oximeters using either mode of operation, for clarity the present invention will only be described in a reflective mode pulse oximeter. However, those skilled in the art will be able to readily adapt the present invention to a transillumination mode instrument.

As previously indicated, (1) the IR LED 28 and the RED LED 30 are mounted in thermal contact with the heat plate 20, and (2) the current control network 50 supplies current to the LEDs 28 and 30 as required, and (3) the heat plate is in contact with a patient's skin. The LEDs 28 and 30 generate heat in an amount proportional to the current through them. This heat is then transferred via the heat plate 20 to the patient's skin. The current control network 50 can supply more current to the LEDs than is required for the basic operation of the pulse oximeter 10. With additional current supplied to the LEDs 28 and 30, additional heat is generated. This heat warms the tissue near the heat plate, causing the flow of blood in the tissue to increase, which increases the electrical signals from the silicon photodiode 32. The warming of the patient's tissue does no occur instantaneously, but rather proceeds over a significant period of time. This time delay between the application of current to the LEDs 28 and 30 and the increase in the electrical signals may require that the heat plate 20 contact the patient's skin for a significant time period before a reliable measurement is obtained.

It is desirable to control the amount of heat applied to the patient's tissue so that sufficient blood flow is present for an accurate measurement, yet below the level that would burn the patient. In the preferred embodiment, the amount of heat generated is measured by the thermistor 34, which varies its resistance as a function of the temperature of the heat plate 20. The resistance of the thermistor 34 is monitored by the current control network 50 which regulates the current through the LEDs to set the temperature of heat plate 20 to an appropriate temperature. The current control network 50 can control the heat generated by varying the magnitude and/or duty cycle of the current through the LEDs 28 and 30. Those skilled in the art will recognize many ways to control the current: analog series pass elements, digital controls, microprocessor based systems, switching supplies, and PROM controls are some of the possibilities.

Figure 3:
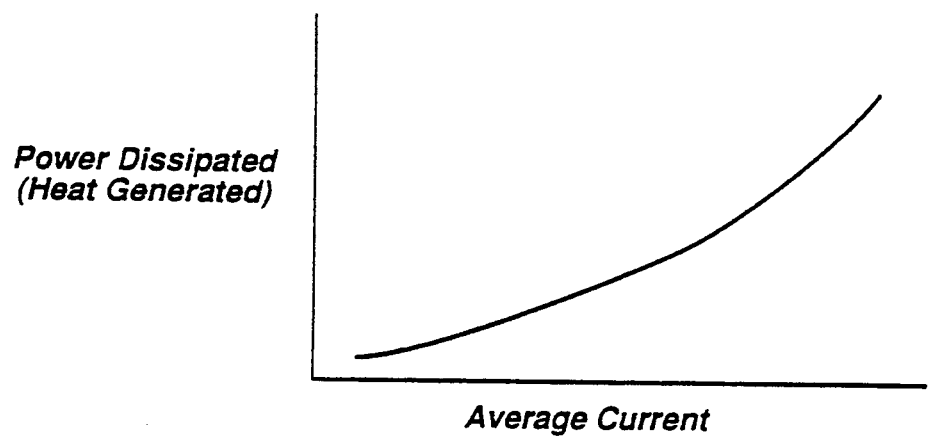
FIG. 3 is a graph showing the relationship between the current through a PN junction and the heat produced at the junction.

The relationship between the heat generated in a PN junction and the current through that junction is better understood by referring to FIG. 3, which is a graph of the power dissipated in a PN junction versus the average current through that junction. The power dissipated is converted into heat. The average current may have a continuous magnitude, or it may be cycled on and off at a rate significantly greater than the thermal time constant of the system so that the heat created is effectively averaged. Note that the curve has a slight upward tilt. This tilt is well known and is caused by the dependency of the forward voltage drop of a semiconductor to the current which causes that forward voltage drop.

Figure 4:
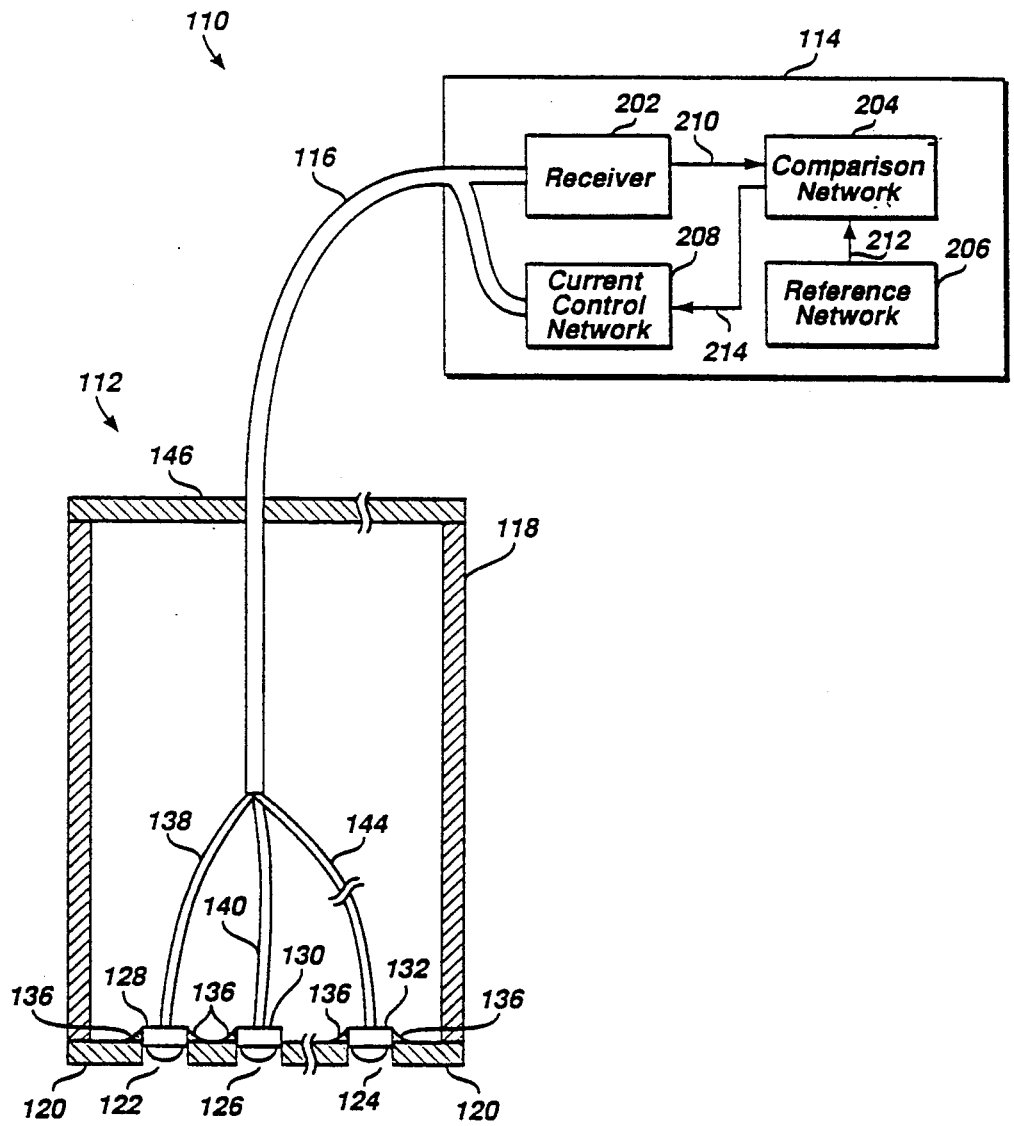
FIG. 4 is a partial cut-away view, partial block diagram of a pulse oximeter which illustrates another embodiment of the present invention.

Another embodiment of the present invention is shown in FIGS. 4 and 5, specifically a pulse oximeter 110 composed of a transducer 112, a pulse oximeter chassis 14, and a cable 116.

The construction and operation of the transducer 12 and the cable 116 are similar to that of the transducer 12 and the cable 16, described previously, except that the thermistor 34 and its associated elements are not present. Therefore, the elements of the transducer 112 and the cable 116 are numbered the same as the corresponding elements in the transducer 12 and the cable 16, except that all numbers are preceded by a 1.

The pulse oximeter chassis 114, however, differs from the pulse oximeter chassis 14. The pulse oximeter chassis 114 has a receiver 202, a comparison network 204, a reference network 206, and a current control network 208. The receiver 202 connects with the comparison network 204 via line 214. The comparison network 204 connects to the reference network 206 via line 212. The current control network 208 connects to the comparison network 204 via line 214.

The interconnections between the transducer 112 and the pulse oximeter chassis 114 are identical to the interconnections between corresponding elements in the pulse oximeter 10, except that the thermistor 34 is no longer present.

In operation, the silicon photodiode 132 creates electrical signals from light reflected from a patient's tissue and blood These electrical signals are applied to the receiver 202, which detects and amplifies them in a conventional manner. The receiver 202 applies its output via line 210 to the comparison network 204, which compares them to a reference signal, on line 212, from the reference network 206.

The reference signal on line 212 corresponds to a desirable output from the receiver 202. The comparison network 204 determines whether the receiver output signals are sufficient for proper pulse oximeter operation. If they are greater than or equal to the reference signal, sufficient blood flow is presumed to exist and additional tissue heating is not required. However, if they are less than the reference signal, the comparison network 204 sends, via line 214, a signal to the current control network 208 which causes the current control network 208 to increase the current to the LEDs 128 and 130, causing additional tissue heating. The current control network 208 may be easily implemented by those skilled in the art using conventional circuit designs. As the tissue warms, the blood circulation increases, causing the receiver output signals to increase. When the receiver output signals equal the reference signal, the comparison network 204 removes the signal on line 214, causing the current control network 208 to reduce the current to the LEDs 128 and 130.

Operation of the embodiment shown in FIGS. 4 and 5 is based on the strong correlations between the receiver output signals and blood flow, and between the tissue temperature and blood flow. These correlations permit the pulse oximeter 110 to determine if additional heat is required, using the receiver output signals to monitor the "relative skin temperature." Relative skin temperature refers not to true temperature, but rather to the effects of temperature on the blood flow.

Many methods are known to those skilled in the art for creating a suitable reference signal: zener diodes, voltage dividers, constant voltage sources, constant current sources, and potentiometers are representative examples. All that is required is that the reference signal be usable by the comparison network 204 to determine if heating is required. Likewise, those skilled in the art will recognize numerous suitable comparison networks, such as operational amplifiers, analog comparators, digital comparators, servomechanisms and schmitt triggers.

While embodiments have been described (1) using a thermistor as a temperature sensor and (2) using the receiver output signal as a "relative skin temperature" sensor, it is contemplated that other temperature-sensing methods are useable with the present invention. Additionally, since it is desirable to avoid burning the patient, temperature limiting controls and limits on the current to the LEDs are specifically contemplated. Finally, while the instant application has been described using light-emitting diodes in a pulse oximeter, other apparatus can also use the principles of the instant invention. Therefore, the present invention is to be protected to the full extent indicated by the broad general meaning of the appended claims.

What is claimed is:

1. An apparatus for increasing blood circulation by heat the tissue of a patient, comprising;
    a housing having a thermally conductive heat plate contacting the tissue;
    a light source generating heat and light in response to current flow therein, said light source being directly mounted on and in thermal contact with an exposed surface of said heat plate so that heat is conducted form said light source directly to said heat plate, said light source;
    sensor means thermally connected to said heat plate, said sensor means applying information on the temperature of said heat plate on an output port; and
    current control means operatively connected to light source and to said output port, said current control means varying current to said light source in response to said temperature information said light source directing light away from said exposed surface of said heat plate so that when the exposed surface of said heat plate is placed in contact with said tissue, said tissue is heated by said heat plate and illuminated by said light source.

2. The apparatus of claim 1 wherein said light source is a light-emitting diode used to perform photoplethysmography.

3. The apparatus of claim 2 wherein said current control means varies the magnitude of current to said light-emitting diode.

4. The apparatus of claim 3 wherein said sensor means includes a thermistor.

5. The apparatus of claim 2 wherein said current control means varies the duty cycle of current to said light-emitting diode.

6. The apparatus of clam 5 wherein said sensor means includes a thermistor.

7. An apparatus for sensing a physical parameter and for increasing blood circulation by heating the tissue of a patient, comprising;
    a housing having a heat plate;
    light emitter diode thermally connected to said heat plate, said light emitter diode generating heat to heat said tissue and light for use in sensing said physical parameter in response to current flow therein;
    a receiver optically connected to said light-emitting diode said receiver creating a received signal from said light from said limit-emitting diode, said received signal being indicative of said physical parameter;
    reference means outputting a reference signal indicative of a desired temperature;
    temperature sensing means generating a temperature signal indicative of the temperature of said heat plate;
    comparison means connected to said temperature signal and to said reference signal, said comparison means comparing said temperature signal to said reference signal and outputting the difference as an error signal; and
    current control means operatively connected to said light emitter diode and to said comparison means, said current control means controlling current flow in said light emitting diode in response to said error signal.

8. The apparatus of claim 7 wherein said current control means aries the magnitude of current to said light-emitting diode.

9. The apparatus of claim 8 wherein said current control means varies the duty cycle of current to said light-emitting diode.

* * * * *

UNITED STATES PATENT AND TRADEMARK OFFICE
CERTIFICATE OF CORRECTION

PATENT NO. : 5,158,082
DATED : October 27, 1992
INVENTOR(S) : Paul H. Jones

Page 1 of 2

It is certified that error appears in the above-indentified patent and that said Letters Patent is hereby corrected as shown below:

In column 5, claim 1, line 68, please delete "heat" and substitute therefor --heating--.

In column 6, claim 1, line 7, please delete "form" and substitute therefor --from--.

In column 6, claim 6, line 32, please delete "clam" and substitute therefor --claim--.

In column 6, claim 7, line 38, please delete "emitter" and substitute therefor --emitting--.

In column 6, claim 7, line 39, please delete "emitter" and substitute therefor --emitting--.

UNITED STATES PATENT AND TRADEMARK OFFICE
CERTIFICATE OF CORRECTION

PATENT NO. : 5,158,082

DATED : October 27, 1992

INVENTOR(S) : Paul H. Jones

It is certified that error appears in the above-identified patent and that said Letters Patent is hereby corrected as shown below:

In column 6, claim 7, line 60, please hyphenate between the words "light" and "emitting".

In column 6, claim 8, line 63, please delete "aries" and substitute therefor --varies--.

Signed and Sealed this

Sixteenth Day of November, 1993

Attest:

BRUCE LEHMAN

*Attesting Officer*     *Commissioner of Patents and Trademarks*